United States Patent
Helal et al.

(10) Patent No.: US 11,529,621 B1
(45) Date of Patent: Dec. 20, 2022

(54) NICKEL-BASED METAL-ORGANIC FRAMEWORK AS CATALYST FOR CHEMICAL FIXATION OF $CO_2$ IN OXAZOLIDINONE SYNTHESIS

(71) Applicant: KING FAHD UNIVERSITY OF PETROLEUM AND MINERALS, Dhahran (SA)

(72) Inventors: Aasif Helal, Dhahran (SA); Mohammed Fettouhi, Dhahran (SA); Md. Eyasin Arafat, Dhahran (SA); Mohd Yusuf Khan, Dhahran (SA); Mohammed Ahmed Sanhoob, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 17/831,961

(22) Filed: Jun. 3, 2022

(51) Int. Cl.
  *B01J 31/16* (2006.01)
  *C07D 263/52* (2006.01)
  *B01J 38/54* (2006.01)
  *C07D 263/22* (2006.01)

(52) U.S. Cl.
  CPC ........... *B01J 31/1691* (2013.01); *B01J 38/54* (2013.01); *C07D 263/22* (2013.01); *C07D 263/52* (2013.01)

(58) Field of Classification Search
  CPC .......................... C07D 263/52; B01J 31/1691
  See application file for complete search history.

(56) References Cited

U.S. PATENT DOCUMENTS 10,233,145 B2  3/2019  Farha et al.

FOREIGN PATENT DOCUMENTS

| CN | 107096569 A | 8/2017 |
|---|---|---|
| CN | 110116024 B | 11/2021 |
| CN | 113617388 A | 11/2021 |
| CN | 109999915 B | 12/2021 |

OTHER PUBLICATIONS

Huang, et al. ; Self-Assembly of CDs@NH2-MOF(Ni)/n-Bu4NBr and its Catalytic Performance for CO2 Fixation with Epoxides ; Australian Journal of Chemistry 74(4) ; pp. 282-289 ; Dec. 24, 2020; Abstract Only ; 1 Page.

Mei, et al. ; Synthesis of Oxazolidinones and Derivatives through Three-Component Fixation of Carbon Dioxide ; ChemCatChem vol. 10, Issue 14 ; pp. 3057-3068 ; Mar. 13, 2018 ; Abstract Only; 1 Page.

*Primary Examiner* — Kamal A Saeed
(74) *Attorney, Agent, or Firm* — Oblon, McClelland, Maier & Neustadt, L.L.P.

(57) ABSTRACT

A method of fixating $CO_2$ to form a substituted oxazolidinone is described. The method includes mixing a nickel-based metal-organic framework (Ni-MOF) catalyst of formula $[Ni_3(BTC)_2(H_2O)_3]\cdot(DMF)_3(H_2O)_3$, a cocatalyst, an aromatic amine, and at least one epoxide to form a reaction mixture, and further contacting the reaction mixture with a gas stream containing carbon dioxide to react the carbon dioxide in the gas stream with the epoxide and the aromatic amine to form a substituted oxazolidinone mixture. The method further includes adding a polar protic solvent to the substituted oxazolidinone mixture, centrifuging, and filtering to produce a recovered Ni-MOF; and further washing the recovered Ni-MOF with an organochloride solvent and drying for at least 5 hours to produce a recycled Ni-MOF.

17 Claims, 8 Drawing Sheets

NICKEL-BASED METAL-ORGANIC FRAMEWORK AS CATALYST FOR CHEMICAL FIXATION OF CO$_2$ IN OXAZOLIDINONE SYNTHESIS

STATEMENT OF PRIOR DISCLOSURE BY THE INVENTOR

Aspects of the present disclosure are described in A. Helal; "Nickel based metal-organic framework as catalyst for chemical fixation of CO$_2$ in oxazolidinone synthesis"; Jun. 5, 2021; Journal of CO$_2$ Utilization, incorporated herein by reference in its entirety.

BACKGROUND

Technical Field

The present disclosure is directed to a metal-organic framework (MOF), and particularly to a nickel-based MOF as a catalyst for chemical fixation of CO$_2$ in oxazolidinone synthesis and a method of preparing the same.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Extensive use of fossil fuels as a primary source of energy in vehicles and industries has steadily increased carbon dioxide (CO$_2$) levels in the atmosphere, resulting in abnormal global climate change. Thus, reducing CO$_2$ emission and fixation of CO$_2$ is the need of the hour. CO$_2$ is inexpensive, abundant, and can be used as the building block for many fine chemicals. But fixation of CO$_2$, which is thermodynamically a stable molecule, in chemical reactions to give value-added products is energy-intensive. Several homogeneous catalysts such as quaternary ammonium salts, ionic liquids, transitional metal complexes, and organo-catalysts have been used to convert the CO$_2$ gas into value-added products, a method known as CO$_2$ fixation. However, such homogeneous catalysts include drawbacks such as recyclability, separation of catalysts, and purification of final products.

One product that can be generated through CO$_2$ fixation is an oxazolidinone, a class of compounds extensively used as an intermediate in organic synthesis of antibacterial, and antimicrobial agents such as tedizolid, linezolid, and radezolid, and also as a key structural unit in pharmaceutical and agrochemical industries. Oxazolidinones are highly important five-membered heterocyclic compounds containing nitrogen and oxygen.

The conventional synthetic method for the synthesis of oxazolidinones uses phosgenes or isocyanates as the source of carbonyl carbon. However, to avoid the toxicity of the starting materials, CO$_2$ or cyclic carbonates can be used as the source of carbonyl in a variety of reactions such as the cycloaddition of CO$_2$ with aziridines, dehydration of vicinal amino alcohols with CO$_2$, cyclization of unsaturated amines with CO$_2$, and the aminolysis of cyclic carbonates. But most of these methods use carbon dioxide under high pressure, use expensive metal catalysts, and are non-recyclable. Very few MOF-based catalysts have been used to synthesize the oxazolidinones, and they are based on the cycloaddition of aziridines to CO$_2$. Therefore, there exists a need for a catalyst and method for the synthesis of oxazolidinones that overcomes the limitations above.

SUMMARY

In an exemplary embodiment, a method of fixating carbon dioxide to form a substituted oxazolidinone is described. The method includes mixing a nickel-based metal-organic framework catalyst of formula [Ni$_3$(BTC)$_2$(H$_2$O)$_3$]·(DMF)$_3$(H$_2$O)$_3$, a cocatalyst, an aromatic amine, and at least one epoxide to form a reaction mixture, and contacting the reaction mixture with a gas stream containing carbon dioxide to react the carbon dioxide in the gas stream with the epoxide and the aromatic amine to form a substituted oxazolidinone mixture.

In some embodiments, nickel-based metal-organic framework catalyst is recyclable for 9 to 20 consecutive cycles.

In some embodiments, the nickel-based metal-organic framework catalyst has an average carbon dioxide uptake of 37 to 60 cc/g at 800 Torr.

In some embodiments, the nickel-based metal-organic framework catalyst has an average isosteric heat of adsorption of 18 to 40 KJmol$^{-1}$.

In some embodiments, the epoxide is selected from a group including epoxy cyclohexane, 1,2-epoxypropane, 1,2-epoxybutane, 1,2-epoxyhexane, styrene oxide, allyl glycidyl ether, and phenyl glycidyl ether.

In some embodiments, the cocatalyst is selected from a group including tetrabutylammonium iodide, tetrabutylammonium bromide, tetrabutylammonium chloride, and tetrabutylammonium fluoride.

In some embodiments, the aromatic amine is at least one selected from a group including aniline, 4-chloroaniline, 4-nitroaniline, toluidine, para-anisidine, and 4-amino thiophenol.

In some embodiments, the reaction mixture has a 1 to 100-500 molar ratio of the cocatalyst to the nickel-based metal-organic framework.

In some embodiments, the reaction mixture has a 1 to 1-5 molar ratio of the nickel-based metal-organic framework to the aromatic amine.

In some embodiments, the method includes contacting the reaction mixture with a gas stream containing carbon dioxide to react the carbon dioxide in the gas stream with the epoxide and the aromatic amine at a temperature of 30 to 160° C. to form a substituted oxazolidinone mixture.

In some embodiments, the method includes contacting the reaction mixture with a gas stream containing carbon dioxide to react the carbon dioxide in the gas stream with the epoxide and the aromatic amine at a temperature of 1 to 15 to form a substituted oxazolidinone mixture.

In some embodiments, the method includes contacting the reaction mixture with a gas stream containing carbon dioxide to react the carbon dioxide in the gas stream with the epoxide and the aromatic amine at a temperature of 5 to 20 hours to form a substituted oxazolidinone mixture.

In some embodiments, 20 to 99% of the aromatic amine is converted into a substituted oxazolidinone.

In some embodiments, 60 to 99% of the aromatic amine is converted into the substituted oxazolidinone with tetrabutylammonium iodide cocatalyst.

In some embodiments, the substituted oxazolidinone has a formula (I); wherein (II)

Formula (I)

where X is selected from a group consisting of an alkyl chain, an allyloxy group, an aromatic group, a methoxybenzene, and cyclohexane; and Y is selected from a group consisting of hydrogen, a halogen, a nitro group, an alkyl chain, a methoxy group, and a thiol.

In some embodiments, the method further includes adding a polar protic solvent to the substituted oxazolidinone mixture, centrifuging, and filtering to produce a recovered nickel-based metal-organic framework; and washing the recovered nickel-based metal-organic framework with an organochloride solvent and drying for at least 5 hours to produce a recycled nickel-based metal-organic framework.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

The present disclosure will be better understood with reference to the following definitions.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

In the drawings, like reference numerals designate identical or corresponding parts throughout the several views. Further, as used herein, the words "a," "an" and the like generally carry a meaning of "one or more," unless stated otherwise. Also, the use of "or" means "and/or" unless stated otherwise. Similarly, "comprise," "comprises," "comprising" "include," "includes," and "including" are interchangeable and not intended to be limiting.

Furthermore, the terms "approximately," "approximate," "about," and similar terms generally refer to ranges that include the identified value within a margin of 20%, 10%, or preferably 5%, and any values there between. For example, if a stated value is about 8.0, the value may vary in the range of 8±1.6, ±1.0, ±0.8, ±0.5, ±0.4, ±0.3, ±0.2, or ±0.1.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The definitions of the terms as used herein are as follows. Unless specified otherwise, these terms are used alone or in combination with another term in the meaning as defined.

As used herein, the terms "optional" or "optionally" means that the subsequently described event(s) can or cannot occur or the subsequently described component(s) may or may not be present (e.g., 0 wt. %).

The term "alkyl", as used herein, unless otherwise specified, refers to a straight, branched, or cyclic, saturated aliphatic fragment having 1 to 26 carbon atoms, (e.g., $C_1$, $C_2$, $C_3$, $C_4$, $C_5$, $C_6$, $C_7$, $C_8$, $C_9$, $C_{10}$, $C_{11}$, etc.) and specifically includes, but is not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-propylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), as well as cyclic alkyl groups (cycloalkyls) such as cyclopropyl, cyclobutyl, cyclopentyl, cyclohexyl, norbornyl, and adamantyl.

The term "aryl" means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, anthracenyl, indanyl, 1-naphthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above) that is substituted by an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "allyloxy", as used herein, unless otherwise specified, refers to an —O—$CH_2$—CH═$CH_2$ group. Exemplary allyoxys that maybe used include (allyloxy)benzene, 3-methyl-allyloxybenzene, 1-allyloxy-2-chloromethylbenzene, 1-(allyloxy)-2-bromobenzene, etc.

The term "epoxide", as used herein, unless otherwise specified, refers to a cyclic ether with a three-atom ring. Exemplary epoxides that maybe used include epoxy cyclohexane, 1,2-epoxypropane, 1,2-epoxybutane, 1,2-epoxyhexane, styrene oxide, allyl glycidyl ether, and phenyl glycidyl ether.

The term "oxazolidinone", as used herein, unless otherwise specified, is a heterocyclic organic compound containing both nitrogen and oxygen in a 5-membered ring.

As used herein, the term "substituted" refers to at least one hydrogen atom that is replaced with a non-hydrogen group, provided that normal valencies are maintained and that the substitution results in a stable compound. When a substituent is noted as "optionally substituted", the substituent(s) are selected from alkyl, halo (e.g., chloro, bromo, iodo, fluoro), hydroxyl, alkoxy, oxo, alkanoyl, aryloxy, alkanoyloxy, amino (—$NH_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkyl sulfonyl, aryl sulfonyl, arylalkylsulfonyl, sulfonamide (e.g., —SO2NH2), substituted sulfonamide (e.g., —$SO_2$NHalkyl, —$SO_2$NHaryl, —$SO_2$NHarylalkyl, or cases where there are two substituents on one nitrogen selected from alkyl, aryl, or alkylalkyl), nitro, cyano, carboxy, unsubstituted amide (i.e. —$CONH_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted, and may be either unprotected, or protected as necessary, as known to those skilled in the art.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

Throughout the specification and the appended claims, a given chemical formula or name shall encompass all isomers (stereo and optical isomers and racemates) thereof where such isomers exist. Unless otherwise indicated, all chiral (enantiomeric and diastereomeric) and racemic forms are within the scope of the disclosure. Many geometric isomers of C═C double bonds, C═N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and salts of products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein "metal-organic frameworks" or MOFs are compounds having a lattice structure made from (i) a cluster of metal ions as vertices ("cornerstones") ("secondary building units" or SBUs) which are metal-based inorganic groups, for example metal oxides and/or hydroxides, linked together by (ii) organic linkers. The linkers are usually at least bidentate ligands which coordinate to the metal-based inorganic groups via functional groups such as carboxylates and/or amines. MOFs are considered coordination polymers made up of (i) the metal ion clusters and (ii) linker building blocks.

Aspects of the present disclosure are directed to a synthesis of a nickel-based Metal-Organic Framework (Ni-MOF) with trimesic acid as a linker. The Ni-MOF was characterized by single-crystal and powder X-ray diffraction (PXRD), Fourier-transform infrared spectroscopy (FT-IR), $N_2$ adsorption isotherm, thermogravimetric analysis (TGA), $CO_2$ adsorption isotherm, and $NH_3$ temperature-programmed desorption (TPD). The synthesized Ni-MOF was further evaluated for its uptake and selectivity for $CO_2$. The results indicate that the Ni-MOF of the present disclosure has a $CO_2$ uptake of 10 to 100, preferably 20 to 80, preferably 30 to 60, preferably 30 to 40, preferably 37 cc/g and a Qst value of 5 to 50, preferably 5 to 30, preferably 10 to 30, preferably 10 to 25, preferably 20.1 $Mmol^{-1}$. The Ni-MOF on activation [Ni-MOF(A)] was used as a heterogeneous catalyst in the fixation of $CO_2$ with epoxide and aromatic amine to synthesize oxazolidinones in an 70 to 95, preferably 75 to 90, preferably 80 to 90, preferably 85% yield. The catalyst of the present disclosure was used under ambient pressure in the presence of tetrabutylammonium iodide (TBAI) as a cocatalyst, obviating the need for high-pressure conditions. The catalyst was also recyclable and can be re-used for nine consecutive cycles.

Figure 1:
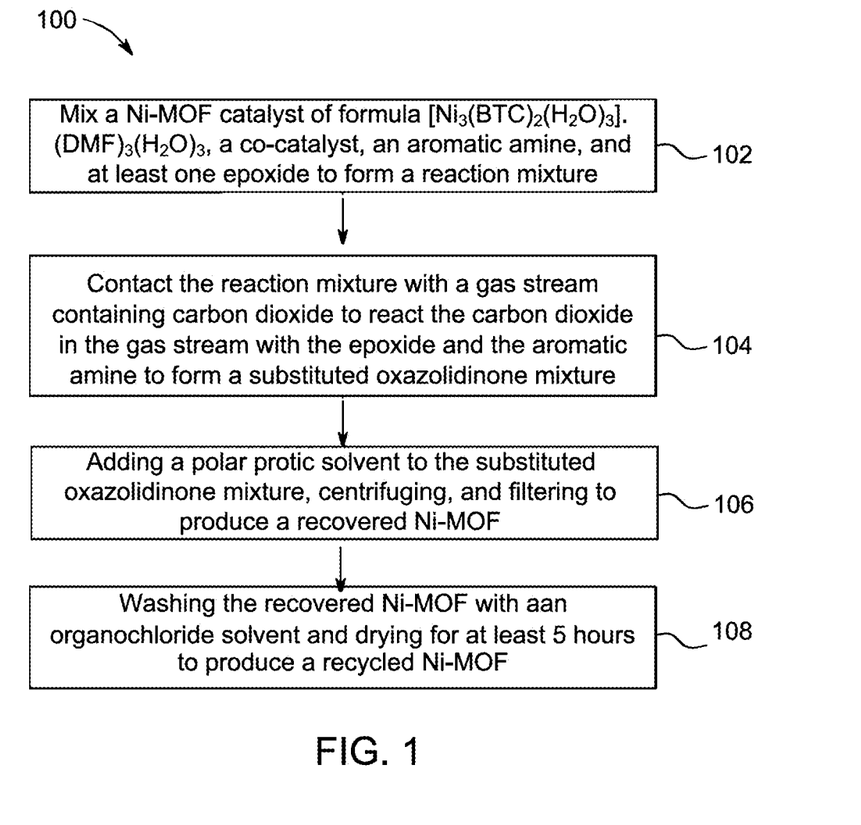
FIG. 1 is a flow chart depicting a method of fixating the carbon dioxide to form a substituted oxazolidinone, according to certain embodiments.

Referring to FIG. 1, a schematic flow diagram of the method of fixating carbon dioxide to form a substituted oxazolidinone is illustrated. The order in which the method 100 is described is not intended to be construed as a limitation, and any number of the described method steps may be combined in any order to implement the method 100. Additionally, individual steps may be removed or skipped from the method 100 without departing from the spirit and scope of the present disclosure.

At step 102, the method 100 includes mixing a Ni-MOF catalyst of formula $[Ni_3(BTC)_2(H_2O)_3]\cdot(DMF)_3(H_2O)_3$, a cocatalyst, an aromatic amine, and at least one epoxide to form a reaction mixture. The reaction mixture has a 1 to 100-500 molar ratio, preferably 1 to 150-450, 1 to 200-400, 1 to 250-350, 1 to 300 of the cocatalyst to the Ni-MOF. In another embodiment, the reaction mixture has a 1 to 1-5 molar ratio of the Ni-MOF to the aromatic amine, preferably 1 to 4, 1 to 3, 1 to 2, or 1 to 1.

In an embodiment, the cocatalyst is selected from a group including tetrabutylammonium iodide, tetrabutylammonium bromide, tetrabutylammonium chloride, and tetrabutylammonium fluoride. In a preferred embodiment, the cocatalyst is TBAI. In an embodiment, the aromatic amine is at least one selected from a group including aniline, 4-chloroaniline, 4-nitroaniline, toluidine, para-anisidine, and 4-amino thiophenol. In an embodiment, the epoxide is selected from a group including epoxy cyclohexane, 1,2-epoxypropane, 1,2-epoxybutane, 1,2-epoxyhexane, styrene oxide, allyl glycidyl ether, and phenyl glycidyl ether.

At step 104, the method 100 includes contacting the reaction mixture with a gas stream containing carbon dioxide to react the carbon dioxide in the gas stream with the epoxide and the aromatic amine to form a substituted oxazolidinone mixture. In some embodiments, the $CO_2$ may be sourced from large fossil fuel or biomass electricity power plants, industries with major $CO_2$ emissions, natural gas processing, synthetic fuel plants, and fossil fuel-based hydrogen production plants. In some embodiments, other possible gasses in the gas stream may include but is not limited to, nitrogen, hydrogen, oxygen, water (vapor), carbon monoxide, hydrocarbons having 1-4 carbon atoms (e.g., methane, ethane, ethylene, acetylene, propane, propylene, butane, iso-butane), nitrogen oxides (i.e., nitric oxide, nitrous oxide, nitrogen dioxide), and noble gases (e.g., helium, neon, argon, krypton, xenon), including mixtures thereof. In some embodiments, the method includes contacting the reaction mixture with a gas stream containing carbon dioxide at a temperature of 10 to 250, preferably 10 to 200, preferably 10 to 180, preferably 20 to 170, preferably 30 to 160° C. to form the substituted oxazolidinone mixture. In some embodiments, the method includes contacting the reaction mixture with a gas stream containing carbon dioxide at a pressure of 1 to 50, preferably 1 to 45, preferably 1 to 30, preferably 1 to 25, preferably 1 to 15 bar of carbon dioxide. In some embodiments, the method includes contacting the reaction mixture with a gas stream containing carbon dioxide for 1 to 50, preferably 1 to 40, preferably 1 to 30, preferably 1 to 25, preferably 5 to 20 hours to form the substituted oxazolidinone mixture. In some embodiments, the method includes contacting the reaction mixture with a gas stream containing carbon dioxide at a temperature of 10 to 300, preferably 10 to 250, preferably 10 to 200, preferably 20 to 180, preferably 30 to 160° C., a pressure of 1 to 50, preferably 1 to 45, preferably 1 to 30, preferably 1 to 25, preferably 1 to 15 bar of carbon dioxide, for 1 to 40, preferably 1 to 30, preferably 1 to 25, preferably 5 to 20 hours, to form the substituted oxazolidinone mixture. In an embodiment, 10 to 99, preferably 13 to 99, preferably 15 to 99, preferably 20 to 99% of the aromatic amine is converted into a substituted oxazolidinone. In another embodiment, 30 to 99, preferably 40 to 99, preferably 50 to 99, preferably 60 to 99% of the aromatic amine is converted into the substituted oxazolidinone with the tetrabutylammonium iodide as the cocatalyst. In an embodiment, the substituted oxazolidinone has a formula (I)

Formula I (II)

where X is selected from a group consisting of an alkyl chain, an allyoxy group, an aromatic group, methoxybenzene, and cyclohexane; and Y is selected from a group consisting of hydrogen, a halogen, a nitro group, an alkyl chain, a methoxy group, and a thiol. The term "aromatic compounds" or "aromatic rings," as used herein, refers to hydrocarbon rings that, by the theory of Hückel, have a cyclic, delocalized (4n+2) pi-electron system. Non-limiting examples of aromatic compounds include benzene, benzene derivatives, compounds having at least one benzene ring in their chemical structure, toluene, ethylbenzene, p-xylene, m-xylene, mesitylene, durene, 2-phenylhexane, biphenyl, phenol, aniline, nitrobenzene, and the like.

At step 106, the method 100 includes adding a polar protic solvent to the substituted oxazolidinone mixture, centrifuging, and filtering to produce a recovered Ni-MOF. The polar protic solvent can include one or more selected from water, ethanol, methanol, ammonia, acetic acid, and other solvents known in the art.

At step 108, the method 100 includes washing the recovered Ni-MOF with an organochloride solvent and drying for at least 5 hours to produce a recycled Ni-MOF. The organochloride solvent is an organic compound bonded covalently to a chlorinated solvent. The chlorinated solvent may be one or more selected from chloroform, dichloromethane, dichloroethene, and trichloroethane, or combinations thereof. The organochloride solvent evaporates on drying, leaving behind the recycled Ni-MOF. The Ni-MOF catalyst is recyclable for 9 to 20 consecutive cycles. No noticeable loss in catalytic activity was observed up to 9 cycles In some embodiments, the Ni-MOF has an average carbon dioxide uptake of 37 to 60 cc/g at 800 Torr. In some embodiments, the Ni-MOF catalyst has a moderate isosteric heat of adsorption of 18 to 40 KJ. $mol^{-1}$.

At step 104, the method 100 includes contacting the reaction mixture with a gas stream containing carbon dioxide to react the carbon dioxide in the gas stream with the epoxide and the aromatic amine to form a substituted oxazolidinone mixture.

EXAMPLES

The following examples describe and demonstrate exemplary embodiments of the nickel-based metal-organic framework as a catalyst for the chemical fixation of $CO_2$ in oxazolidinone synthesis as described herein. The examples are provided solely for illustration and are not to be construed as limitations of the present disclosure, as many variations thereof are possible without departing from the spirit and scope of the present disclosure.

Example 1: Crystal Structure

Figure 2:
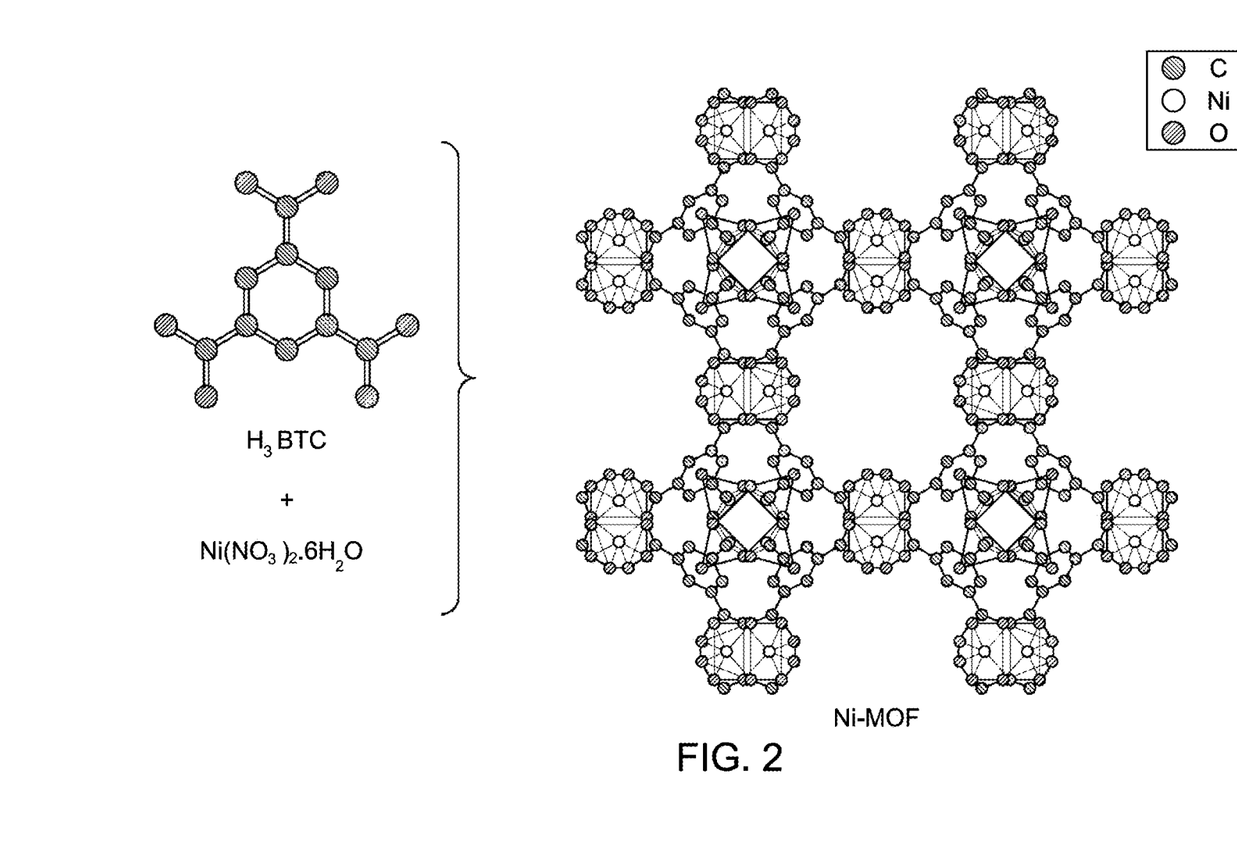
FIG. 2 is a schematic representation of Ni-metal organic framework (MOF), according to certain embodiments.

The Ni-MOF of formula $[Ni_3(BTC)_2(H_2O)_3](DMF)_3$ $(H_2O)_3$, (Cambridge Structural Database deposit number 1965212) is iso-structural to the reported Cu-MOF $[Cu_3(BTC)_2(H_2O)_3]$(HKUST-1) and the Ni-MOF $(Ni_3(BTC)_2(Me_2NH)_3]\cdot(DMF)_4$ $(H_2O)_4$. The three-dimensional framework structure is of cubic symmetry Fm-3m. It is based on the paddle-wheel secondary building unit (SBU): $[Ni_2(H_2O)_2(CO_2^-)_4]$ and the tripodal BTC linker. Four equatorial carboxylate ligands bridge two pentacoordinate Nickel (II) ions in the SBU unit. Each metal ion is additionally bonded to an axial aqua ligand in a distorted square pyramidal geometry (FIG. 2). The large central cavity extends into microporous channels in three dimensions. Using the atomic centers of the aqua ligand oxygen atoms as the points of a square, the edge of the square was found to be 6.056 Å and 8.564 Å across its diagonal. The total potential solvent-accessible volume, as determined using the PLATON/VOID routine, was about 65.3%.

Figure 3:
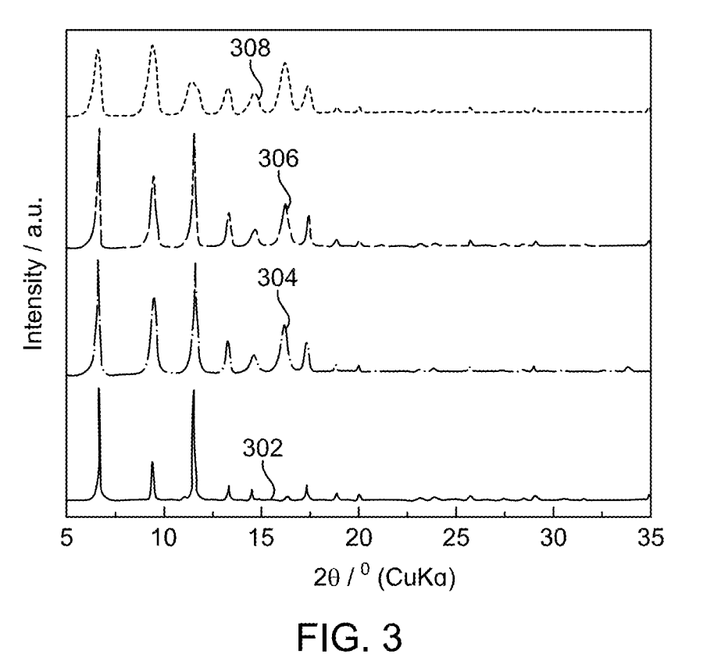
FIG. 3 is a powdered X-ray diffraction (XRD) pattern of the Ni-MOF, according to certain embodiments.
Figure 4:
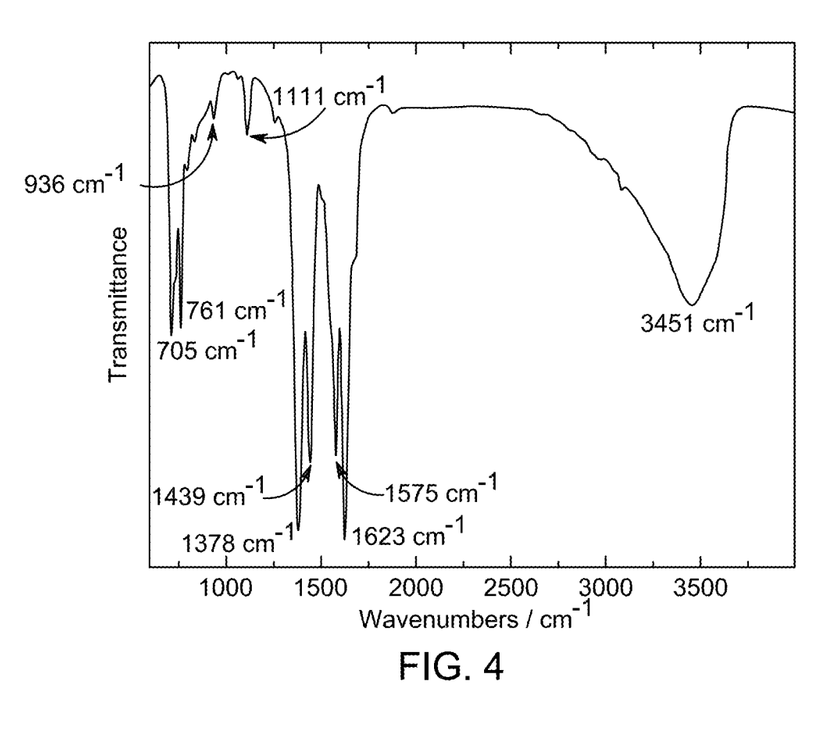
FIG. 4 is a Fourier Transform Infrared (FT-IR) spectrum of the Ni-MOF, according to certain embodiments.
Figure 5:
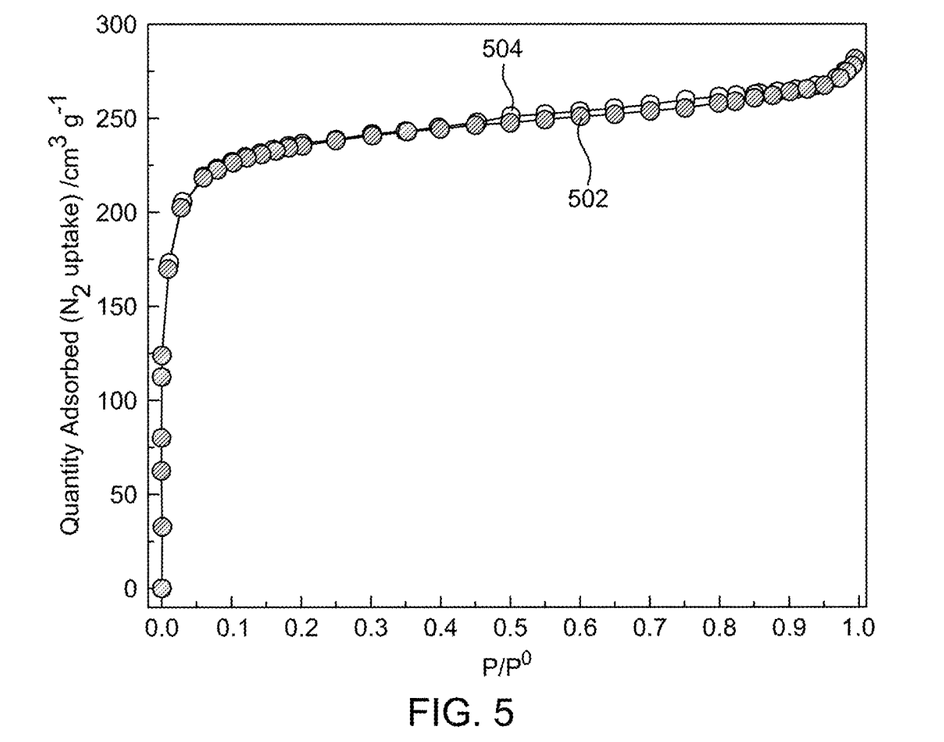
FIG. 5 depicts a nitrogen adsorption isotherm of the Ni-MOF, according to certain embodiments.

The powder X-ray diffraction (PXRD) analysis confirmed the crystallinity and the phase purity of the Ni-MOF by comparing the experimental diffraction patterns to that of the diffraction patterns simulated from the single crystal structure (FIG. 3). The prominent characteristic peaks at 6.7°, 9.4°, 11.5, and 13.3° were consistent in the simulated Ni-MOF (302), as-synthesized Ni-MOF (304), and the activated form of Ni-MOF or "Ni-MOF (A)" (306) and Ni-MOF (A) after the $9^{th}$ cycle (308) which validates that activation does not disturb the connectivity and framework of the Ni-MOF. The Fourier transform infrared spectrum is given in FIG. 4. The bands at 705 $cm^{-1}$ and 761 $cm^{-1}$ are assigned to the out-of-plane aromatic C—H bending modes of the linker. The band at 1111 $cm^{-1}$ is assigned to the aromatic C—H in-plane bending. The strong bands (1378, 1439 $cm^{-1}$) and (1575, 1623 $cm^{-1}$) are likely due to the symmetric and asymmetric C—O stretching modes of the $COO^-$ group, respectively. The broad band centered at 3451 $cm^{-1}$ corresponds to the O—H stretching vibrations of the coordinated and solvation water molecules. The $N_2$ adsorption isotherm (adsorption of Ni-MOF (A) (502) and desorption of Ni-MOF (A) (504)) at 77K divulged that the Ni-MOF is microporous in nature with Type I isotherm (FIG. 5). The Brunauer-Emmett-Teller surface area was calculated to be 858 $m^2/g$.

Figure 6:
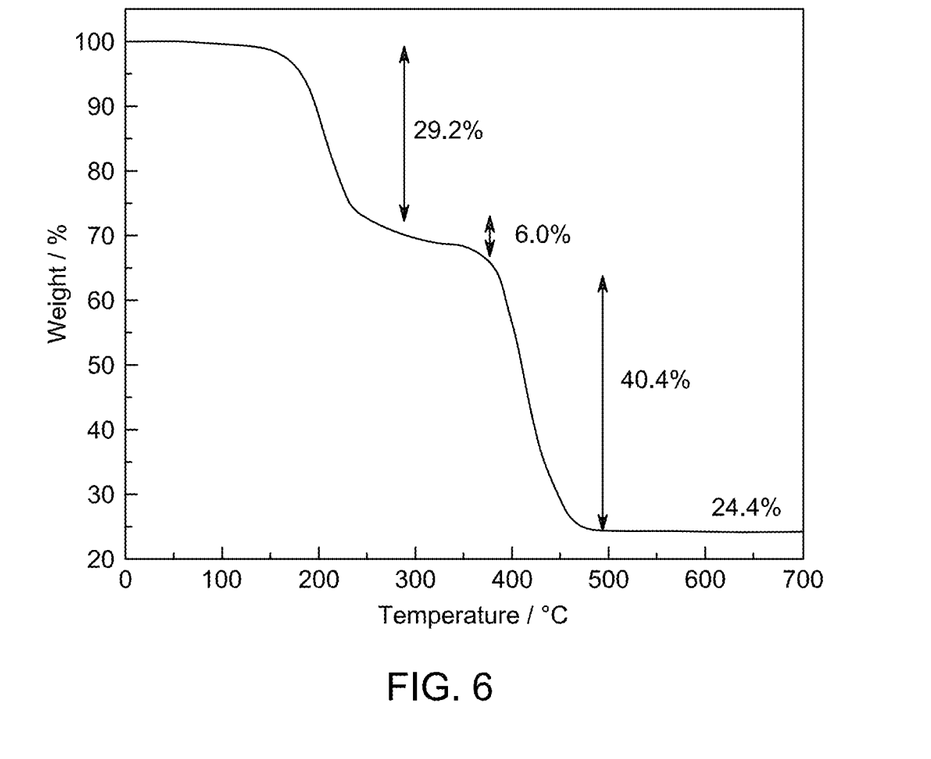
FIG. 6 depicts a thermogravimetric analysis (TGA) curve of the Ni-MOF, according to certain embodiments.

Thermogravimetric analysis was carried out to determine the thermal stability of the Ni-MOF; the results of this study are depicted in FIG. 6, From FIG. 6, there were three stages of weight loss. (i) in the first stage, there is a weight loss of 29.2% at 200° C. due to the loss of water and solvent molecules trapped in the pores of the framework. The calculated weight loss of 3 DMF and 3 water molecules per formula $\{[Ni_3(BTC)_2(H_2O)_3]\cdot(DMF)_3(H_2O)_3\}$ corresponds to 29.8%. (ii) The second stage is a continuous weight loss of about 6.0% from 200-390° C. was attributed to the evacuation of the coordinated water molecules. The calculated weight loss of three coordinated water molecules per formula corresponds to 5.9%. (iii) The third stage shows an abrupt weight loss of about 40.4% at 390-500° C., which is assigned to the total thermal decomposition of the framework. The final residue of 24.4% is attributed to the formation of nickel oxide.

Figure 7:
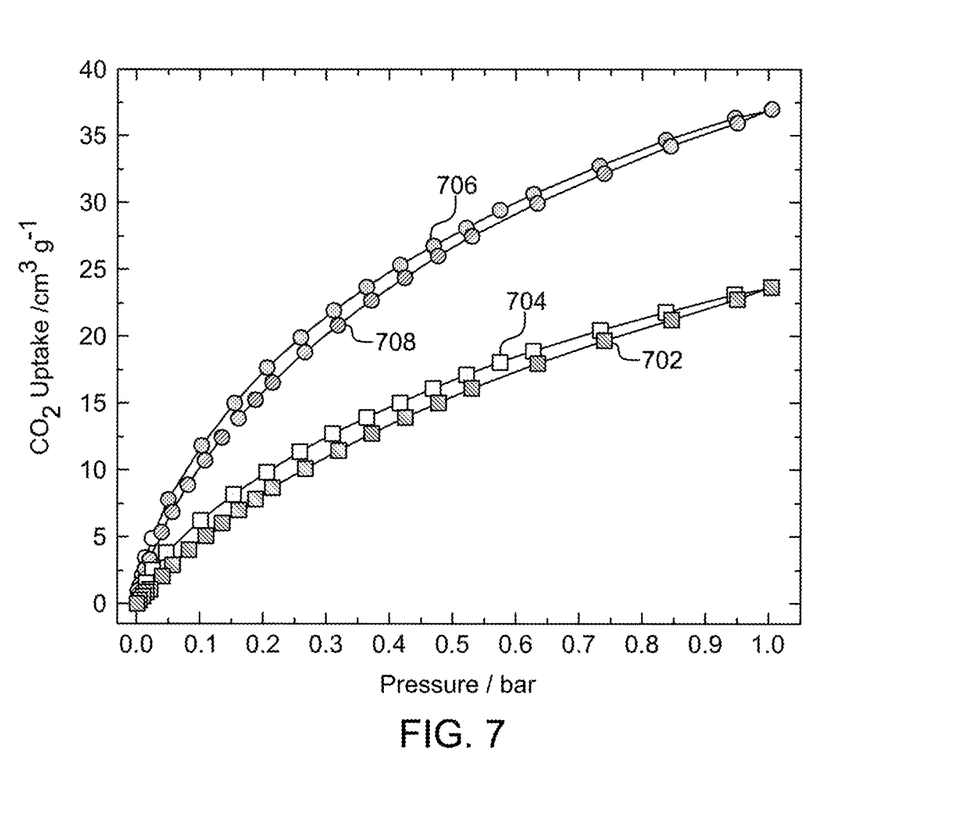
FIG. 7 depicts a $CO_2$ adsorption-desorption isotherm for the Ni-MOF, according to certain embodiments.

Further, the $CO_2$ adsorption isotherm of the Ni-MOF at two different temperatures of 273 K and 298 K was investigated to determine the $CO_2$ adsorption capability of the MOF. FIG. 7 depicts the $CO_2$ adsorption at 273 K (708), $CO_2$ desorption at 273 K (706), $CO_2$ adsorption at 298 K (702), and $CO_2$ desorption at 298 K (704). From FIG. 7, it was observed that the $CO_2$ uptake was abated as usual with the increase in the temperature; maximum $CO_2$ uptake for the Ni-MOF was found to be 37 cc/g at 273 K and 23 cc/g at 298 K at 1 bar or 800 Torr. To understand the nature of Ni-MOF interaction with $CO_2$, the coverage-dependent $CO_2$ adsorption enthalpies of the Ni-MOF were calculated from the $CO_2$ isotherms obtained at 273 K and 298 K by using the Clausius-Clapeyron equation. The adsorption enthalpy or the isosteric heat of adsorption for the Ni-MOF was calculated to be 20.1 kJ $mol^{-1}$.

Catalysis for the synthesis of oxazolidinones from aromatic amines, epoxides, and $CO_2$ To check the activity of the Ni-MOF as a catalyst, a three-component reaction of aniline, 1,2-epoxypropane, and $CO_2$ as a model was used to determine the desired reaction conditions, including the type of cocatalysts to be used to maximize the conversion to the model oxazolidinone (Table 1).

TABLE 1 cycloaddition reaction of $CO_2$ with aniline and 1,2-epoxypropane in the presence of catalysts

| Entry | Catalyst | Cocatalysts | Yield of C1 (%)[b] |
|---|---|---|---|
| 1 | $Ni(NO_3)_2 \cdot 6H_2O$ | None | No reaction |
| 2 | $Ni(NO_3)_2 \cdot 6H_2O$ | TBAI | 11 |
| 3 | Ni-MOF | None | 15 |
| 4 | Ni-MOF | TBAI | 22 |
| 5 | Ni-MOF(A) | TBAI | 85 |
| 6 | Ni-MOF(A) | TBABr | 45 |
| 7 | Ni-MOF(A) | TBACl | 32 |
| 8 | Ni-MOF(A) | TBAF | 21 |

[a] Reaction conditions: 1,2-epoxypropane (10.0 mmol), aniline (2.0 mmol), solvent-free, catalyst (60 mg), $CO_2$ (1 bar), 12 h, 90 °C.
[b] Isolated yield calculated with respect to A It was detected that $Ni(NO_3)_2$ alone could not produce any product with $CO_2$ at 1 bar pressure, a temperature of 90° C., and a reaction time of 12 h (Entry 1 Table 1). However, in the presence of the cocatalyst tetrabutylammonium iodide (TBAI) under the same reaction conditions, a minimal amount of the product (11%) was formed (Entry 2, Table 1). The introduction of Ni-MOF as a catalyst with the same reaction conditions produces a low yield of the product with (22%) or without (15%) the cocatalysts (Entry 3, 4, Table 1). The final product yield augmented to 85% when Ni-MOF was activated (Entry 5, Table 1). This was due to the removal of water and solvents attached to the active metal centers in the MOF, leading to CUS (coordinatively unsaturated sites) exposure that enhanced the Lewis acidity of the MOF (Table 1) responsible for the catalysis.

The catalytic activities of the Ni-MOF(A) with different tetrabutylammonium salts of bromide; chloride, and fluoride were studied; however, their yields were as low as 45%, 32%, and 21%, respectively, in comparison to tetrabutylammonium iodide (85%) (Entry 6, 7, and 8, Table 1). This is ascribed to a strong leaving group and nucleophilic nature of the iodide ion compared to the bromide, chloride, and fluoride ion, enabling the tetrabutylammonium iodide to enhance the reaction rate.

To explore this catalyst's versatility with reference to different amine-based substrates, reactions with various para-substituted aromatic amines were conducted under desired conditions, and the results are compiled in Table 2 with their turnover number (TON) and turnover frequency (TOF).

To explore this catalyst's versatility with reference to different amine-based substrates, reactions with various para-substituted aromatic amines were conducted under desired conditions, and the results are compiled in Table 2 with their turnover number (TON) and turnover frequency (TOF). The study revealed that aniline with an electron-withdrawing group such as ($-NO_2$) and ($-Cl$) gave a higher yield of 95% and 90%, respectively (Entry 2, and 5, Table 2) as compared to the aniline with an electron-donating group ($-CH_3$ yield 81%, $-OCH_3$ yield 79%, and $-SH$ yield 75%) (Entry 3, 4, and 6 Table 2).

TABLE 2

Cycloaddition reaction of $CO_2$ with different aromatic amines and 1,2-epoxypropane in the presence of Ni-MOF$_{(A)}$ as catalysts[a]

| Entry | Aromatic amine | Product | Yield (%)[b] | TON/TOF (h$^{-1}$) |
|---|---|---|---|---|
| 1 | A1 | C1 | 85 | 609/50.8 |
| 2 | A2 | C2 | 95 | 681/56.8 |
| 3 | A3 | C3 | 81 | 581/48.4 |

TABLE 2-continued

Cycloaddition reaction of $CO_2$ with different aromatic amines and 1,2-epoxypropane in the presence of Ni-MOF$_{(A)}$ as catalysts[a]

| Entry | Aromatic amine | Product | Yield (%)[b] | TON/TOF (h$^{-1}$) |
|---|---|---|---|---|
| 4 | A4 (H$_3$CO–C$_6$H$_4$–NH$_2$) | C4 | 79 | 566/47.2 |
| 5 | A5 (Cl–C$_6$H$_4$–NH$_2$) | C5 | 90 | 645/53.8 |
| 6 | A6 (HS–C$_6$H$_4$–NH$_2$) | C6 | 75 | 538/44.8 |

[a]Reaction conditions: 1,2-epoxypropane (10.0 mmol), aromatic amine (2.0 mmol), solvent-free, catalyst (60 mg), $CO_2$ (1 bar), 12 h, 90 °C., tetrabutylammonium iodide as co-catalysts.
[b]Isolated yield calculated with respect to A. Determined by $^1$H NMR spectroscopy. All the products had 100% selectivity.

Further, this catalyst's applicability was also checked with different epoxides, and the results of this study are summarized in Table 3 along with TON and TOF. It can be observed from Table 3 that all the monosubstituted aliphatic and aromatic epoxides gave a good yield of oxazolidinone with aniline (yield 85-78%). The reaction proceeded smoothly with bulky disubstituted epoxides such as cyclohexane oxide in the presence of this catalyst giving the corresponding oxazolidinone in 70% yield.

TABLE 3

Cycloaddition reaction of $CO_2$ with different epoxides and aniline in Ni-MOF(A) as a catalyst[a]

| Entry | Epoxide | Product | Yield (%)[b] | TON/TOF (h$^{-1}$) |
|---|---|---|---|---|
| 1 | B2 | C7 | 83 | 595/49.6 |
| 2 | B3 | C8 | 80 | 574/47.8 |
| 3 | B4 | C9 | 81 | 581/48.4 |

TABLE 3-continued

Cycloaddition reaction of CO₂ with different epoxides and aniline in Ni-MOF(A) as a catalyst[a]

| Entry | Epoxide | Product | Yield (%)[b] | TON/TOF (h⁻¹) |
|---|---|---|---|---|
| 4 |  B5 |  C10 | 78 | 559/46.6 |
| 5 |  B6 |  C11 | 85 | 609/50.8 |
| 6 |  B7 |  C12 | 70 | 502/41.8 |

[a]Reaction conditions: Epoxides (10.0 mmol), aniline (2.0 mmol), solvent-free, catalyst (60 mg), CO₂ (1 bar), 12 h, 90 °C., tetrabutylammonium iodide as cocatalysts.
[b]Isolated yield calculated with respect to A. Determined by ¹H NMR spectroscopy. All the products had 100% selectivity.

Further, it was observed that in all the cases, the reaction yielded only the 5-substituted oxazolidinones and not 4-substituted oxazolidinones or a mixture of two, probably as a result of steric hindrance between the aromatic amines, the epoxide side chain, with the catalyst of the present disclosure. Further, the product was characterized by $^1$H NMR and $^{13}$C NMR spectra, and the identities of the oxazolidinones were confirmed by correlation with literature. There was no reaction with the aliphatic amines in forming the oxazolidinones using Ni-MOF(A). This was probably due to aliphatic amine being more basic in nature, preferably binding with the active site of the nickel in the Ni-MOF, preventing the ring-opening of the epoxides.

Figure 8:
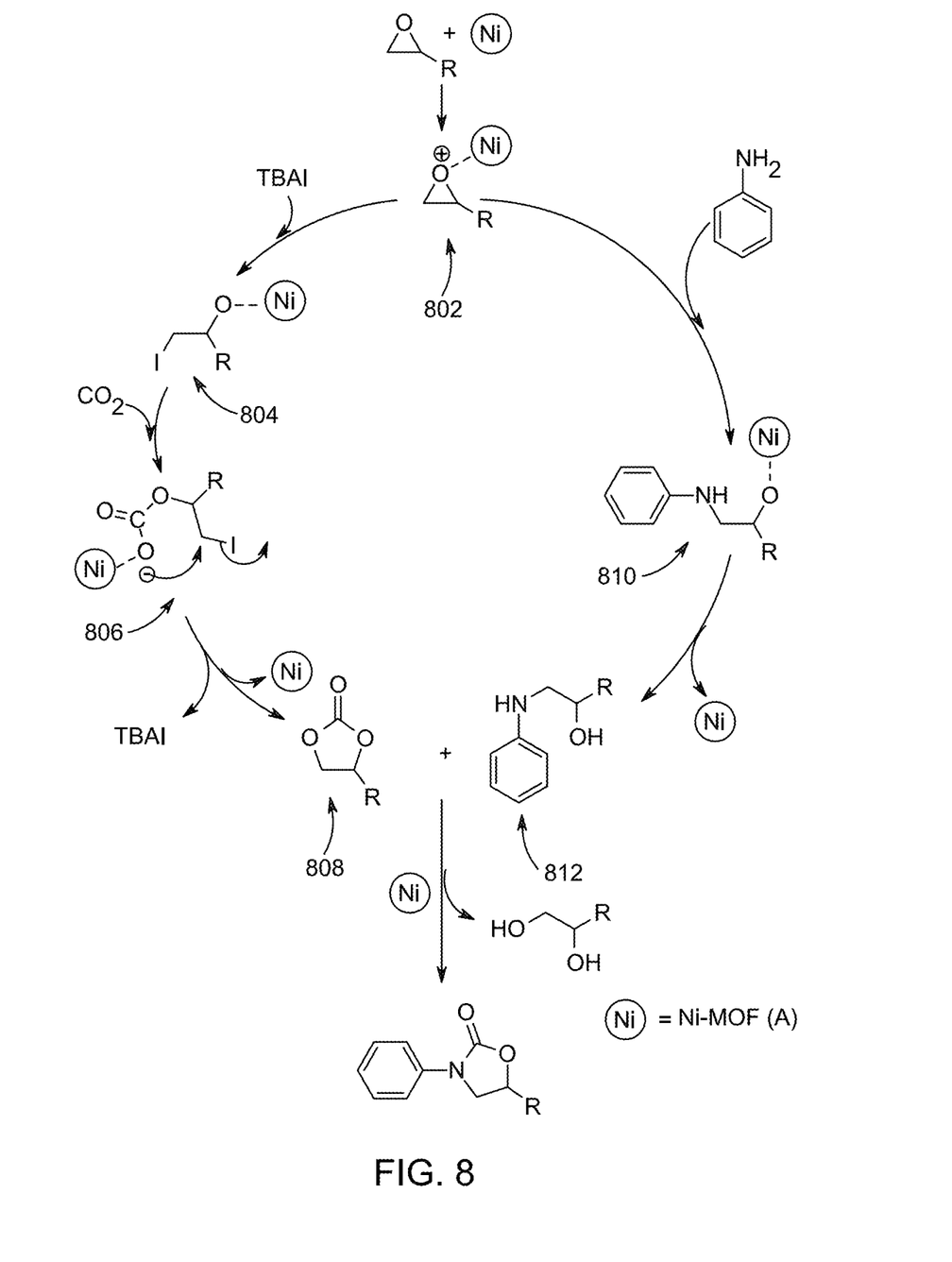
FIG. 8 depicts a plausible mechanism for the formation of the oxazolidinone, according to certain embodiments.

Further, the mechanism of formation of the oxazolidinones is given in FIG. 8. From the activated MOF structure, it can be concluded that the nickel clusters have exposed coordinatively unsaturated sites (CUS) that can act as Lewis's acid. The epoxide was activated by the exophilic Ni cluster of the Ni-MOF(A) to form the adduct (802). This is followed by the nucleophilic attack of the bulky iodide ion of the TBAI on the less impeded carbon of the epoxide ring leads to the opening of the three-membered epoxide ring to form (804). A nucleophilic attack by the carbon dioxide on the oxygen of the open epoxy ring (804) results in an alkyl carbonate anion (806). Consequently, iodide being a better leaving group result in the ring-closing and formation of the corresponding cyclic carbonate (808) with the regeneration of the catalysts. The adduct (802) also undergoes nucleophilic addition reaction with the aniline to form (810), consequently forming the corresponding β-amino alcohol (812). Compounds 808 and 812 interact with each other in the presence of the Ni-MOF(A) to form the corresponding oxazolidinone and 1,2-diol as a byproduct. The intermediates 808 and 812 were separately synthesized, and $^1$HNMR confirmed their structures. In addition, a similar experiment in the presence of argon, aniline, 1,2-epoxy propane, TBAI, and Ni-MOF(A) was conducted that resulted in the formation of the intermediate 812 (β-amino alcohol). This concludes that CO₂ is essential in the formation of oxazolidinones.

Figure 9:
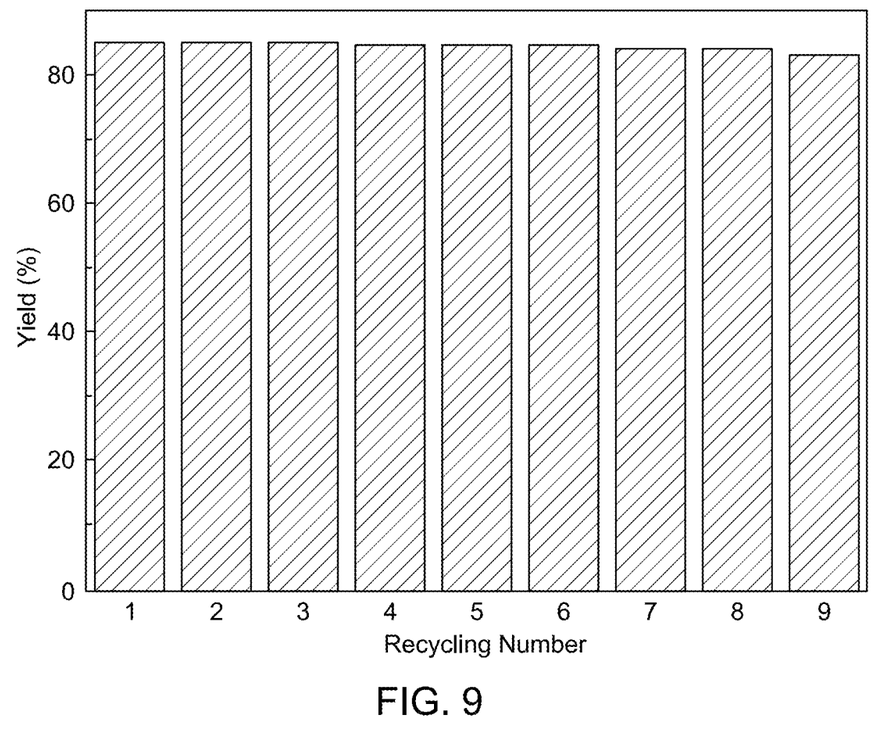
FIG. 9 depicts recycle tests with Ni-MOF for the reaction of $CO_2$ with aniline and 1,2-epoxypropane to form oxazolidinone, according to certain embodiments.

Recyclability is an essential facet of heterogeneous catalysis. Ni-MOF(A) can be quickly recovered after completion of the reaction from the reaction mixture by centrifugation and then washed with IMF and dichloromethane consecutively three times each. The catalysts were again activated by heating the MOF at 150° C. in a vacuum oven for 6 h. The recycling performance of Ni-MOF(A) was studied, which confirmed that this catalyst could be re-used for nine cycles without any noticeable loss in catalytic activity (FIG. 9), The ICP-MS of the Ni-MORA) showed negligible change in the nickel content before and after reaction, confirming that no nickel leaching occurred during catalysis. The bands in the FT-IR spectrum of Ni-MOF before and after use in catalysis were similar, indicating that the MOF is stable during catalysis. Moreover, the Ni-MOF obtained after catalytic reaction exhibits a similar N₂ isotherm profile as the MOF before catalysis with a slight decrease in the N₂ adsorption volume.

A porous Ni-MOF was synthesized with a CO₂ uptake of 37 cc/g. On thermal activation, it generates coordinatively unsaturated active metal sites that act as a Lewis acid in the CO₂ fixation with epoxides and aromatic amines in the synthesis of oxazolidinone in the presence of TBAI as a cocatalyst. The catalyst was used under ambient pressure, and solvent-free conditions are recyclable for nine cycles and do not produce extra byproducts. The catalyst was successfully applied for various epoxides and aromatic amines with good yield.

Numerous modifications and variations of the present disclosure are possible in light of the above teachings. Therefore, it is to be understood that within the scope of the appended claims, the invention may be practiced otherwise than as specifically described herein.

The invention claimed is:

1. A method of fixating carbon dioxide to form a substituted oxazolidinone, comprising:
    mixing a nickel-based metal organic framework catalyst of formula $[Ni_3(BTC)_2(H_2O)_3]\cdot(DMF)_3(H_2O)_3$, a cocatalyst, an aromatic amine, and at least one epoxide to form a reaction mixture; and
    contacting the reaction mixture with a gas stream containing carbon dioxide to react the carbon dioxide in the gas stream with the epoxide and the aromatic amine to form the substituted oxazolidinone.

2. The method of claim 1, wherein the nickel-based metal organic framework catalyst is recyclable for 9 to 20 consecutive cycles.

3. The method of claim 1, wherein the nickel-based metal organic framework catalyst has an average carbon dioxide uptake of 37 to 60 cc/g at 800 Torr.

4. The method of claim 1, wherein the nickel-based metal organic framework catalyst has an average isosteric heat of adsorption of 18 to 40 KJ. $mol^{-1}$.

5. The method of claim 1, wherein the epoxide is selected from a group comprising of epoxycyclohexane, 1,2-epoxypropane, 1,2-epoxybutane, 1,2-epoxyhexane, styrene oxide, allyl glycidyl ether, and phenyl glycidyl ether.

6. The method of claim 1, wherein the cocatalyst is selected from a group comprising of tetrabutylammonium iodide, tetrabutylammonium bromide, tetrabutylammonium chloride, and tetrabutylammonium fluoride.

7. The method of claim 1, wherein the aromatic amine is at least one selected from a group consisting of aniline, 4-chloroaniline, 4-nitroaniline, toluidine, para-anisidine, and 4-aminothiophenol.

8. The method of claim 1, wherein the reaction mixture has a 1 to 100-500 molar ratio of the cocatalyst to the nickel-based metal organic framework.

9. The method of claim 1, wherein the reaction mixture has a 1 to 1-5 molar ratio of the nickel-based metal organic framework to the aromatic amine.

10. The method of claim 1, wherein the contacting occurs at a temperature of 30 to 160° C.

11. The method of claim 1, wherein the contacting occurs at a pressure of 1 to 15 bar of carbon dioxide.

12. The method of claim 1, wherein the contacting occurs for 5 to 20 hours.

13. The method of claim 1, wherein 20 to 99% of the aromatic amine is converted into the substituted oxazolidinone.

14. The method of claim 13, wherein 60 to 99% of the aromatic amine is converted into the substituted oxazolidinone with tetrabutylammonium iodide cocatalyst.

15. The method of claim 1, wherein the substituted oxazolidinone has a formula (I); wherein (II)

X is selected from a group consisting of an alkyl chain, an allyoxy group, an aromatic group, a methoxybenzene, and a cyclohexane; and Y is selected from a group consisting of a hydrogen, a halogen, a nitro group, an alkyl chain, a methoxy group, and a thiol.

16. The method of claim 1, further comprising:
    adding a polar protic solvent to the substituted oxazolidinone mixture, centrifuging, and filtering to produce a recovered nickel-based metal organic framework; and
    washing the recovered nickel-based metal organic framework with an organochloride solvent and drying for at least 5 hours to produce a recycled nickel-based metal organic framework.

17. The method of claim 15, wherein the contacting forms only a 5-substituted oxazolidinone.

* * * * *